(12) United States Patent
Wehner et al.

(10) Patent No.: US 7,829,736 B2
(45) Date of Patent: *Nov. 9, 2010

(54) METHOD FOR THE PRODUCTION OF CYCLIC PHOSPHONIC ACID ANHYDRIDES

(75) Inventors: Mark Wehner, Niedernhausen (DE); Bettina Kirschbaum, Turnhout (BE); Lothar Deutscher, Schwalbach (DE); Hans Jürgen Wagner, Hattersheim (DE); Harald Hössl, Kelkheim (DE)

(73) Assignee: Archimica GmbH, Frankfurt am Main (DE)

( * ) Notice: Subject to any disclaimer, the term of this patent is extended or adjusted under 35 U.S.C. 154(b) by 242 days.

This patent is subject to a terminal disclaimer.

(21) Appl. No.: 12/061,124

(22) Filed: Apr. 2, 2008

(65) Prior Publication Data

US 2008/0183009 A1 Jul. 31, 2008

Related U.S. Application Data

(62) Division of application No. 10/565,470, filed on Jan. 20, 2006, now Pat. No. 7,473,794.

(30) Foreign Application Priority Data

Jul. 21, 2003 (DE) ............................... 103 33 042

(51) Int. Cl.
C07F 9/02 (2006.01)
(52) U.S. Cl. ........................................................ 558/83
(58) Field of Classification Search ................... 558/83
See application file for complete search history.

(56) References Cited

U.S. PATENT DOCUMENTS

| | | | |
|---|---|---|---|
| 4,195,035 A | 3/1980 | Dursch | |
| 5,191,065 A | 3/1993 | Flemming | |
| 5,319,138 A | 6/1994 | Roscher | |
| 6,407,258 B1 | 6/2002 | Holla | |
| 7,473,794 B2 * | 1/2009 | Wehner et al. | 558/83 |

FOREIGN PATENT DOCUMENTS

| | | |
|---|---|---|
| DE | 100 63493 | 6/2002 |
| JP | 54-98724 A1 | 3/1979 |
| JP | 60-218399 A1 | 1/1985 |
| JP | 1-279921 A1 | 11/1989 |
| JP | 5-209057 A1 | 8/1993 |
| JP | 6-86478 A1 | 2/1994 |
| JP | 9-157284 A1 | 6/1997 |
| WO | WO99/37620 | 6/1999 |

OTHER PUBLICATIONS

English language Abstract for DE 100 63493, Jun. 27, 2002.
H. Wissmann et al., "New Peptide Synthesis", Angew. Chem Int. Ed (1980), 19, pp. (133-134).
V. Brandmeier et al., "2'-Aminomethylbiphenyl-2-caronsaeure als Bestandteil eines Cyclopeptids", Angew. Chem, (1989), 28, 486, pp. (466-468).
M. Wedel et al., "Synthesis of Metalloporphyrins and Metallochlorins for Immobilization of Electrode Surfaces", Eur. J. Org. Chem, (2001), pp. (1681-1687).

O.N. Grishna, et al., "Anhydrides of Alkyl- Cycloalkyl-, and Arylphosphonic Acids", Jour of Gen Chem USSR, (1976), 46(7), pp. (1458-1460).
K. Diemert, et al., "A Convenient Synthesis of Phosphonic Anhydrides—Trimers: Their Structure and Reaction Products", Eur. J. Inorg Chem, (1998), pp. (361-366).
S.H. Metzger, et al., Highly Branched Alkylphosphorous Compounds, Synthesis of 1,1,2-Trimethylpropylphosphonyl Chloride, J. Org. Chem, vol. 29, No. 3 (1964), pp. (627-630).
PCT International Search Report, Feb. 23, 2005, in connection with Application PCT/EP2004/007468.
Watanabe et al. 1992, CAS: 116:132130.
Ueda, M. et al.: "Synthesis of Polyamides by Direct Polycondensation with Propylphosphonic Anhydride as an Activating Agent" Polymer Journal, vol. 20, No. 6, pp. 477-483, 1988.

* cited by examiner

Primary Examiner—Rei-tsang Shiao
(74) Attorney, Agent, or Firm—ProPat, L.L.C.

(57) ABSTRACT

Method of performing condensation reactions, acylations or of preparing heterocycles comprising forming cyclic phosphonic anhydride of the formula (III) by a) reacting phosphonic acid derivatives of formula (I) with acetic anhydride at a temperature ranging between 30 and 150° C. while separating a mixture of ethanoic acid and acetic anhydride by means of distillation, b) then reactively distilling the oligomeric phosphonic acid anhydrides of formula (II) obtained in step a) and transforming the same into the corresponding cyclic trimeric phosphonic acid anhydrides of formula (III), wherein n represents a number between 0 and 300 while R represents allyl, aryl, or open-chain, cyclic, or branched C1 to C8 alkyl radicals, aryloxy, allyloxy, or alkoxy comprising open-chain, cyclic, or branched C1 to C8 alkyl radicals. Preferably the cyclic trimeric phosphonic acid anhydrides formed in step b) are immediately dissolved in an organic solvent that exhibits an inert behavior relative thereto.

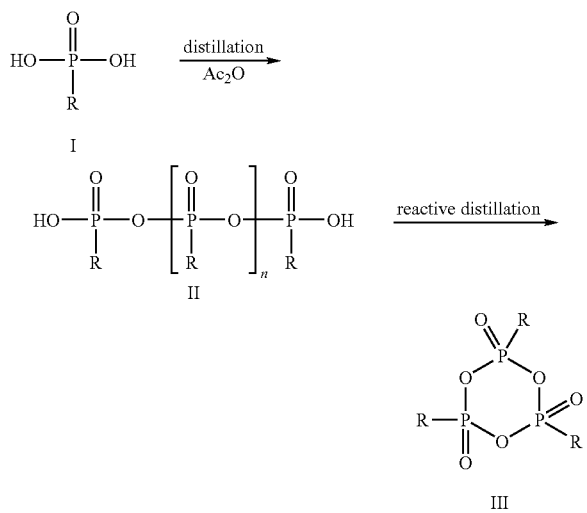

10 Claims, No Drawings

METHOD FOR THE PRODUCTION OF CYCLIC PHOSPHONIC ACID ANHYDRIDES

CROSS-REFERENCE TO RELATED APPLICATIONS

This divisional application claims priority to parent application Ser. No. 10/565,470, filed Jan. 20, 2006, now U.S. Pat. No. 7,473,794 hereby incorporated by reference herein in its entirety.

FIELD OF THE INVENTION

The present invention relates to an improved process for preparing known 2,4,6-substituted 1,3,5,2,4,6-trioxatriphosphinane 2,4,6-trioxides (III) from the parent phosphonic acids of the formula (I) via their open-chain analogs of the formula (II) by distillation.

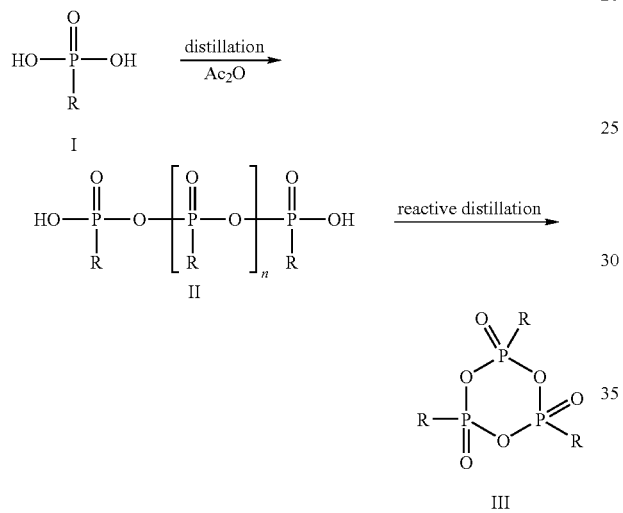

BACKGROUND OF THE INVENTION

The preparation of the oligomeric phosphonic anhydrides of the formula (II) (OPA) by condensation with a suitable assistant (EP-B-0 527 442) and the use of these OPAs to form amide bonds (DE-A-38 39 379) is already known.

However, to form amide bonds, it is necessary here in accordance with the state of the art to use excesses of OPA because, in the product prepared according to EP 0 527 442, phosphonic anhydrides of chain length $P_{20}$-$P_{200}$ are prepared and the composition of the OPA is thus not known precisely. Resulting costs can be avoided by virtue of the cyclic propanephosphonic anhydrides of the formula (III) (CPA) prepared by the process according to the invention.

Phosphonic acids are degraded by microorganisms typically to the phosphate, which is ecologically problematic (eutrophication). The use of the cyclic phosphonic anhydrides (CPA), which is reduced because it is stoichiometric, can prevent this. This achieves a further advantage by the preparation and the use of compounds of the formula (III) compared to the known preparation processes and applications, as described in EP-A-0 527 442 and EP-A-3 839 379.

The selected preparation of CPAs in the laboratory has already succeeded (H. Wissmann, H. J. Kleiner, Angew. Chem. Int. Ed. 1980, 19, 133 [129]). The possibility of a distillation of the CPAs is mentioned here, but it is an additional purifying distillation of CPAs already present as crude products. Moreover, in this process, the CPAs are prepared using phosphonyl dichlorides.

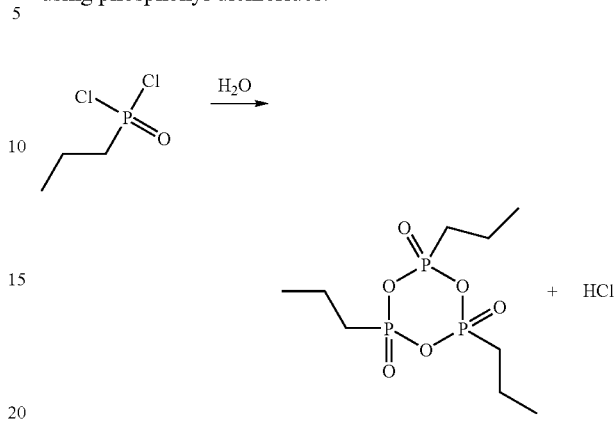

The HCl formed in this preparation process poses many problems in an industrial application of this synthesis route as a result of its corrosive and toxic properties. An additional fact is that the product comprises chloride, which can restrict the possible uses of the CPAs.

With regard to the aforementioned disadvantages of the known processes, in which a product mixture is obtained in undefined composition, large amounts of waste occur, corrosive and toxic gases form or the product comprises chloride, there is a need to provide an improved process which does not have all of these disadvantages.

BRIEF SUMMARY OF ADVANTAGEOUS EMBODIMENTS OF THE INVENTION

This object is achieved by a process for preparing cyclic phosphonic anhydrides of the formula (III) by a) reaction of phosphonic acid alkanes of the formula (I) with acetic anhydride at a temperature in the range from 30 to 150° C. and simultaneous distillative removal of a mixture of acetic acid and acetic anhydride, b) subsequent reactive distillation of the oligomeric phosphonic anhydrides of the formula (II) obtained in step a) and conversion to the corresponding cyclic trimeric phosphonic anhydrides of the formula (III)

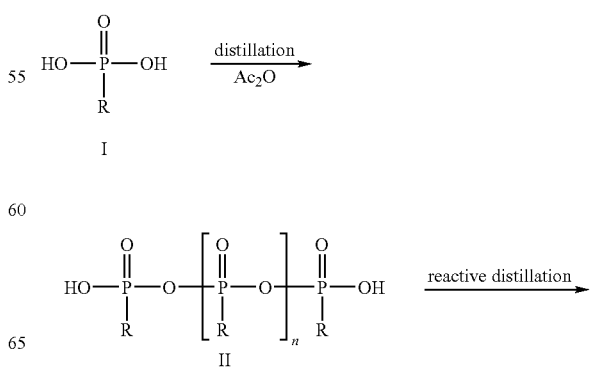

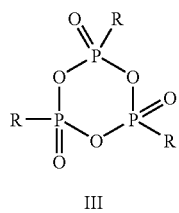

III c) the cyclic trimeric phosphonic anhydrides formed preferably being dissolved immediately in an organic solvent which is inert toward them, where n is an integer from 0 to 300 and R are H, fluorine, chlorine, bromium, iodine, allyl, aryl or open-chain or branched $C_1$ to $C_8$-alkyl radicals, aryloxy, allyloxy or alkoxy having open-chain or branched $C_1$ to $C_8$-alkyl radicals, nitro, nitrile, carboxy, carboxylic esters having open-chain or branched $C_1$ to $C_8$-alkyl radicals, amide or alkylamide radicals having open-chain or branched $C_1$ to $C_8$-alkyl radicals.

DETAILED DESCRIPTION OF ADVANTAGEOUS EMBODIMENTS OF THE INVENTION

In the process according to the invention, the OPAs of the formula (II) obtained in step a) are converted directly to CPAs of the formula (II) by a reactive distillation and, immediately after they are obtained, dissolved in a suitable solvent. In this way, it is possible to prevent immediate polymerization of the CPAs to reform the oligomeric phosphonic anhydrides.

Suitable solvents are those which do not react with the phosphonic anhydrides, these in particular being aprotic organic solvents.

Suitable solvents are all aprotic organic solvents which do not react with the CPA of the formula (III), preference being given to ligroin, pentane, hexane, heptane, octane, cyclopentane, cyclohexane, cycloheptane, cyclooctane, dichloromethane, chloroform, carbon tetrachloride, 1,2-dichloroethane, 1,1,2,2-tetrachloroethane, methyl acetate, ethyl acetate, propyl acetate, butyl acetate, dimethylformamide, diethylformamide, dimethylacetamide, diethylacetamide, diethyl ether, diisopropyl ether, tert-butyl methyl ether, THF, dioxane, acetonitrile, sulfolane, DMSO, HMPT, NMP or mixtures thereof, particular preference to dichloromethane, chloroform, ethyl acetate, propyl acetate, butyl acetate, dimethylformamide, diethylformamide, dimethylacetamide, diethylacetamide, diisopropyl ether, tert-butyl methyl ether, THF, dioxane, acetonitrile or mixtures thereof, very particular preference to dichloromethane, chloroform, ethyl acetate, butyl acetate, dimethylformamide, dimethylacetamide, tert-butyl methyl ether, THF, dioxane, acetonitrile or mixtures thereof.

During the reactive distillation, after the full distillative removal of acetic acid and unconverted acetic anhydride under reduced pressure, the present OPA of the formula (II) (preparation analogous to EP-B-0 527 442) is dissociated at a vacuum of from 0.001 mbar to 500 mbar and a temperature of from 100° C. to 450° C. to obtain CPAs of the formula (III) in pure form.

The process according to the invention has the particular feature that, in contrast to the processes known to date, only a low level of apparatus complexity is required, since the preparation of the OPAs of the formula (II) and the reactive distillation to prepare the CPAs of the formula (III) can be carried out in the same reaction vessel.

It should be regarded as very surprising that the formation of the cyclic compounds (III) succeeds by a reactive distillation. The selected conditions in the distillation can afford the desired CPA in pure form; no reoligomerization takes place.

As mentioned above, suitable R radicals in the formula (I), (II) and (III) are allyl, aryl or open-chain cyclic or branched $C_1$ to $C_8$-alkyl radicals, aryloxy, allyloxy or alkoxy having open-chain cyclic or branched $C_1$ to $C_8$-alkyl radicals. Particularly suitable radicals are those where R=methyl, ethyl, n-propyl, isopropyl, n-butyl, 2-butyl, isobutyl, pentyl, hexyl; very particularly suitable are ethyl, propyl and butyl radicals.

The ratio of acetic anhydride to the phosphonic acid of the formula (I) can be selected as desired, but should not be too small and is preferably in the range between 20:1 and 1:1, more preferably between 10:1 and 1:1 and most preferably between 5:1 and 1:1.

The reaction and distillation in the process according to the invention takes place in two stages, and comprises a) the condensation of phosphonic acids of the formula (I) to give OPAs of the formula (II) with simultaneous distillation of acetic acid and unconverted acetic anhydride in a temperature range from 30° C. to 150° C. (internal reactor temperature) or from 30° C. to 130° C. (top temperature), but preferably in the temperature range from 50° C. to 130° C. (the internal reactor temperature) or from 35° C. to 100° C. (top temperature), most preferably in the temperature range from 70° C. to 110° C. (the internal reactor temperature) or from 40° C. to 70° C. (top temperature), and b) the reactive distillation of the OPA of the formula (II) to give CPA of the formula (III), which is effected in the temperature range of 100° C. and 450° C. (the internal reactor temperature) or from 100° C. to 380° C. (top temperature), but preferably in temperature range of 150° C. and 400° C. (the internal reactor temperature) or from 150° C. to 350° C. (top temperature), more preferably in the temperature range of 200° C. and 350° C. (the internal reactor temperature) or from 200° C. to 300° C. (top temperature).

In the process according to the invention, the pressure in a) the distillation of acetic acid and unconverted acetic anhydride is in the range from 1 mbar and 1000 mbar, preferably in the range from 10 mbar to 500 mbar, more preferably in the range from 50 mbar to 200 mbar, and in b) the reactive distillation of the OPA of the formula (II) to give CPA of the formula (III) is within a pressure range from 0.001 mbar to 500 mbar, preferably in the range from 0.005 mbar to 100 mbar, more preferably in the range from 0.01 mbar to 50 mbar.

The distillation may be effected over any period; frequently, a) the distillation of acetic acid and acetic anhydride takes place, however, within 100 h, preferably within 80 h, more preferably within 60 h, and b) the reactive distillation of OPA of the formula (II) to CPA of the formula (III) within 120 h, preferably within 90 h, more preferably within 60 h.

It has generally been observed that the distillation and the reactive distillation can be carried out on small scales within a relatively short period, while the reaction times increase on conversion, for example, to the pilot-plant scale.

The resulting CPA of the formula (III) is dissolved in an organic solvent immediately after the distillation; the mixing ratio between solvent and CPA may be selected as desired, but should not be selected at too low a level owing to the viscosity of the compound, and is preferably in the range of 10:1 and 1:10, more preferably in the range of 5:1 and 1:5, most preferably in the range of 2:1 and 1:2. In a preferred embodiment, the CPA condensate is collected directly in the inert organic solvent in order to prevent polymerization and reformation to give the analogous oligomers.

The thus prepared solution of CPA of the formula (III) and the selected solvent or solvent mixture can be used directly for condensation reactions such as amide formations (M. Feigel et al., Angew. Chem. Int. Ed. 1989, 28, 486 [466]) and ester formations (F. -P. Montforts et al., Eur. J. Org. Chem. 2001, 1681-1687), acylations (DE 100 63 493) and for the preparation of heterocycles (WO 99/37620).

In particular, the process according to the invention has the advantage over the prior art that a compound of the formula (III) of defined molar mass is formed from the different oligomers of the formula (II) and can thus be used in stoichiometric amounts. This increases the economic viability of the use of these phosphonic anhydrides in chemical processes, for example in condensation reactions of carboxylic acids with alcohols or amines. The dissolution of the syrupy compound in an organic solvent allows it to be handled particularly easily and it can surprisingly also be used directly in a multitude of reactions in this form.

The thus obtained solutions can in particular form amide bonds and the coupling reagent can be added in a defined and sparing amount.

The examples and comparative examples which follow serve to illustrate the subject matter of the invention without any intention that the invention be restricted to these examples.

EXAMPLES

Example 1

Synthesis of 2,4,6-tripropyl-[1,3,5,2,4,6]-trioxatriphosphinane 2,4,6-trioxide

In a glass flask with stirrer, stopper, internal thermometer and distillation column, 33.0 g of propanephosphonic acid (0.27 mol) are dissolved under argon in 189.3 g of acetic anhydride (1.85 mol) and heated to reflux for 2 h. Subsequently, the mixture of acetic acid and acetic anhydride is distilled off at 100 mbar. The external temperature is increased to 350° C. and the vacuum to 0.1 mbar. At top temperature 280° C., 22.9 g of colorless, syrupy 2,4,6-tripropyl-[1,3,5,2,4,6]-trioxatriphosphinane 2,4,6-trioxide are obtained (yield 80%).

The thus obtained CPA is dissolved in 22.9 g of dichloromethane and can be used for further synthesis in this form.

Example 2

Synthesis of 2,4,6-tripropyl-[1,3,5,2,4,6]-trioxatriphosphinane 2,4,6-trioxide

In a glass flask with stirrer, stopper, internal thermometer and distillation column, 33.0 g of propanephosphonic acid (0.27 mol) are dissolved under argon in 189.3 g of acetic anhydride (1.85 mol) and heated to reflux for 2 h. Subsequently, the mixture of acetic acid and acetic anhydride is distilled off at 100 mbar. The external temperature is increased to 350° C. and the vacuum to 0.1 mbar. At top temperature 280° C., 22.9 g of colorless, syrupy 2,4,6-tripropyl-[1,3,5,2,4,6]-trioxatriphosphinane 2,4,6-trioxide are obtained (yield 80%).

The thus obtained CPA is dissolved in 22.9 g of dimethylformamide and can be used for further synthesis in this form.

Example 3

Synthesis of 2,4,6-triethyl-[1,3,5,2,4,6]-trioxatriphosphinane 2,4,6-trioxide

In a glass flask with stirrer, stopper, internal thermometer and distillation column, 40.2 g of ethanephosphonic acid (0.37 mol) are dissolved under argon in 204.9 g of acetic anhydride (2.01 mol) and heated to reflux for 2 h.

Subsequently, the mixture of acetic acid and acetic anhydride is distilled off at 100 mbar. The external temperature is increased to 350° C. and the vacuum to 0.1 mbar. At top temperature 295° C., 20.2 g of colorless, syrupy 2,4,6-triethyl-[1,3,5,2,4,6]-trioxatriphosphinane 2,4,6-trioxide are obtained (yield 66%).

Example 4

Synthesis of 2,4,6-trihexyl-[1,3,5,2,4,6]-trioxatriphosphinane 2,4,6-trioxide

In a glass flask with stirrer, stopper, internal thermometer and distillation column, 44.8 g of hexanephosphonic acid (0.27 mol) are dissolved under argon in 189.3 g of acetic anhydride (1.85 mol) and heated to reflux for 2 h. Subsequently, the mixture of acetic acid and acetic anhydride is distilled off at 100 mbar. The external temperature is increased to 350° C. and the vacuum to 0.1 mbar. At top temperature 240° C., 30.0 g of colorless, syrupy 2,4,6-trihexyl-[1,3,5,2,4,6]-trioxatriphosphinane 2,4,6-trioxide are obtained (yield 75%).

The thus obtained CPA is dissolved in 30 g of dichloromethane and can be used for further synthesis in this form.

Example 5

Synthesis of 2,4,6-tricyclohexyl-[1,3,5,2,4,6]-trioxatriphosphinane 2,4,6-trioxide In a glass flask with stirrer, stopper, internal thermometer and distillation column, 44.3 g of cyclohexylphosphonic acid (0.27 mol) are dissolved under argon in 189.3 g of acetic anhydride (1.85 mol) and heated to reflux for 2 h. Subsequently, the mixture of acetic acid and acetic anhydride is distilled off at 100 mbar. The external temperature is increased to 350° C. and the vacuum to 0.1 mbar. At top temperature 260° C., 27.6 g of colorless, syrupy 2,4,6-tricyclohexyl-[1,3,5,2,4,6]-trioxatriphosphinane 2,4,6-trioxide are obtained (yield 70%).

The thus obtained CPA is dissolved in 27.6 g of dichloromethane and can be used for further synthesis in this form.

Example 6

Synthesis of N-acetyl-L-phenylalaninyl-L-alanine Methyl Ester 0.1 g of L-alanine methyl ester hydrochloride (0.7 mmol), 0.2 g of N-acetyl-L-phenylalanine (1 mmol) and 0.55 ml of N-methylmorpholine (5 mmol) are dissolved in 50 ml of dichloromethane and cooled to −10° C. 0.5 g of CPA from example 1 (50% in $CH_2Cl_2$; 0.8 mmol) is added slowly, and the mixture is stirred under cold conditions for 3 h and at room temperature for 72 h. The solution is concentrated by evaporation and extracted with ethyl acetate and 1N HCl solution, sat. NaHCO₃, sat. NaCl and dist. water. The organic phase is dried over magnesium sulfate, filtered off and concentrated by evaporation. 0.18 g of the white N-acetyl-L-phenylalaninyl L-alanine methyl ester is obtained (88%).

Example 7

Synthesis of
N-acetyl-L-phenylalaninyl-L-phenylalanine Methyl Ester 0.38 g of L-phenylalanine methyl ester hydrochloride (1.8 mmol), 0.37 g of N-acetyl-L-phenylalanine (1.7 mmol) and 1.6 ml of N-methylmorpholine (14.6 mmol) are dissolved in 30 ml of dimethylacetamide and cooled to 0° C. 1.2 ml of CPA from example 2 (50% in dimethylformamide, 1.9 mmol) are then added. The mixture is stirred at 0° for another 1 h and at room temperature for 12 h. The solution is concentrated by evaporation and extracted with ethyl acetate and 1N HCl solution, sat. NaHCO₃, sat. NaCl and dist. water. The organic phase is dried over magnesium sulfate, filtered off and concentrated by evaporation. 0.53 g of the white N-acetyl-L-phenylalaninyl-L-phenylalanine methyl ester is obtained (84%).

Comparative Example 8

Synthesis of
N-acetyl-L-phenylalaninyl-L-phenylalanine Methyl Ester with the Same Amount of OPA as in Example 5

0.38 g of L-phenylalanine methyl ester hydrochloride (1.8 mmol), 0.37 g of N-acetyl-L-phenylalanine (1.7 mmol) and 1.6 ml of N-methylmorpholine (14.6 mmol) are dissolved in 30 ml of dimethylacetamide and cooled to 0° C. 1.2 ml of OPA, prepared as described in EP 0 527 442, example 1 (50% in dimethylformamide, molar amount not possible because the composition is not known) are then added. The mixture is stirred at 0° C. for another 1 h and at room temperature for 12 h. The solution is concentrated by evaporation and extracted with ethyl acetate and 1N HCl solution, sat. NaHCO₃, sat. NaCl and dist. water. The organic phase is dried over magnesium sulfate, filtered off and concentrated by evaporation. 0.14 g of the white N-acetyl-L-phenylalaninyl-L-phenylalanine methyl ester is obtained (22%).

Comparative Example 9

Synthesis of
N-acetyl-L-phenylalaninyl-L-phenylalanine Methyl Ester with an Increased Amount of OPA in Comparison to Example 5

0.38 g of L-phenylalanine methyl ester hydrochloride (1.8 mmol), 0.37 g of N-acetyl-L-phenylalanine (1.7 mmol) and 5.0 ml of N-methylmorpholine (45.5 mmol) are dissolved in 30 ml of dimethylacetamide and cooled to 0° C. 5 ml of OPA, prepared as described in EP 0 527 442, example 1 (50% in dimethylformamide, molar amount not possible because the composition is not known) are then added. The mixture is stirred at 0° C. for another 1 h and at room temperature for 12 h. The solution is concentrated by evaporation and extracted with ethyl acetate and 1N HCl solution, sat. NaHCO₃, sat. NaCl and dist. water. The organic phase is dried over magnesium sulfate, filtered off and concentrated by evaporation. 0.55 g of the white N-acetyl-L-phenylalaninyl-L-phenylalanine methyl ester is obtained (87%).

What is claimed is:

1. A method of performing condensation reactions, acylations or of preparing heterocycles comprising forming cyclic phosphonic anhydride of the formula (III) by
    a) reaction of a phosphonic acid derivative of the formula (I) with acetic anhydride at a temperature in the range from 30 to 150° C. and simultaneous distillative removal of a mixture of acetic acid and acetic anhydride,
    b) subsequent reactive distillation of the oligomeric phosphonic anhydride of the formula (II) obtained in step a) and conversion to the corresponding cyclic trimeric phosphonic anhydride of the formula (III)

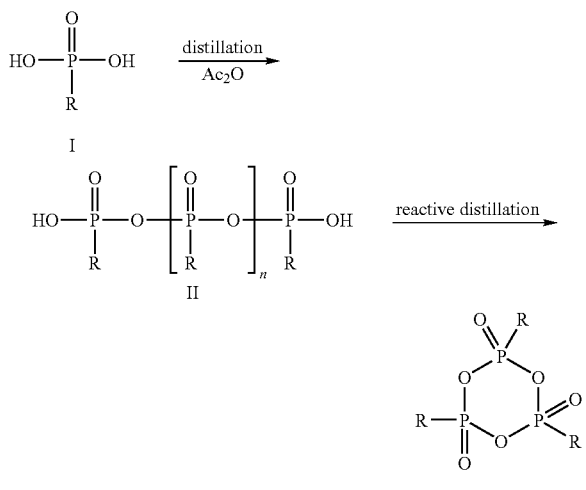

where
    n is an integer from 0 to 300 and
    R are allyl, aryl or open-chain cyclic or branched $C_1$ to $C_8$-alkyl radicals, aryloxy, allyloxy or alkoxy having open-chain cyclic or branched $C_1$ to $C_8$-alkyl radicals.

2. The method as claimed in claim 1, wherein the cyclic trimeric phosphonic anhydride formed in step b) is immediately dissolved in an organic solvent which is inert toward said cyclic trimeric phosphonic anhydride.

3. The method as claimed in claim 1, wherein the ratio of acetic anhydride to phosphonic acid of the formula (I) is in the range of 20:1 and 1:1.

4. The method as claimed in claim 1, wherein the reactive distillation in step b) is effected at a temperature in the range from 100 to 450° C. (the internal reactor temperature) and a top temperature of from 100 to 380° C.

5. The method as claimed in claim 1, wherein the pressure in
    a) the distillation of acetic acid and unconverted acetic anhydride is between 1 mbar and 1000 mbar, and
    b) in the reactive distillation of the oligomeric phosphonic anhydride of the formula (II) to give the cyclic phosphonic anhydride of the formula (III) is within a pressure range between 0.001 mbar and 500 mbar.

6. The method as claimed in claim 1, wherein said process for forming cyclic phosphonic anhydride is carried out continuously.

7. The method as claimed in claim 1, wherein the cyclic trimeric phosphonic anhydride of the formula (III), after the reactive distillation, is dissolved in an organic solvent in a mixing ratio of solvent to phosphonic anhydride in the range of 10:1 and 1:10.

8. The method as claimed in claim 7, wherein the organic solvent is selected from ligroin, sulfolane, DMSO, HMPT, NMP, pentane, hexane, heptane, octane, cyclopentane, cyclohexane, cycloheptane, cyclooctane, dichloromethane, chloroform, carbon tetrachloride, 1,2-dichloroethane, 1,1,2,2-tetrachloroethane, methyl acetate, ethyl acetate, propyl acetate, butyl acetate, dimethylformamide, diethylformamide, dimethylacetamide, diethylacetamide, diethyl ether, diisopropyl ether, tert-butyl methyl ether, THF, dioxane, acetonitrile, sulfolane, DMSO, HMPT, NMP, or a mixture thereof.

9. The method as claimed in claim 1, wherein R is an open-chain, cyclic or branched $C_1$ to $C_8$-alkyl radical.

10. The method as claimed in claim 1, wherein said cyclic phosphonic anhydride of the formula (III) is prepared by
   a) reaction of a phosphonic acid derivative of the formula (I) with acetic anhydride at a temperature in the range from 30 to 150° C. and simultaneous distillative removal of a mixture of acetic acid and acetic anhydride, and
   b) subsequent reactive distillation of the oligomeric phosphonic anhydride of the formula (II) obtained in step a) and conversion to the corresponding cyclic trimeric phosphonic anhydride of the formula (III)

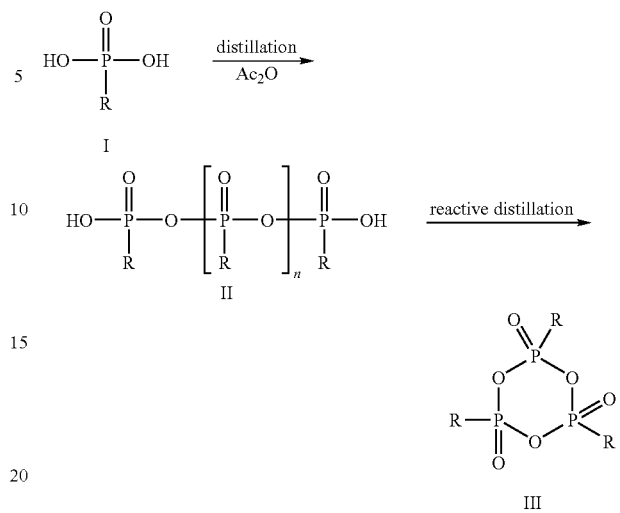

where
n is 1 and
R is propyl.

* * * * *